(12) United States Patent
Geldenhuys et al.

(10) Patent No.: US 11,304,835 B2
(45) Date of Patent: Apr. 19, 2022

(54) INFLATABLE INSERTION DEVICE FOR PERCUTANEOUS INSERTION

(71) Applicant: STRAIT ACCESS TECHNOLOGIES HOLDINGS (PTY) LTD, Cape Town (ZA)

(72) Inventors: Giuseppe Geldenhuys, Cape Town (ZA); Fourie Gildenhuys, Cape Town (ZA); Braden Sydney Clive Van Breda, Cape Town (ZA); Kenneth Stuart Park, Wynberg (ZA); Carl Nick Van Zyl, Cape Town (ZA); Jandré De Villiers, Cape Town (ZA); Peter Paul Zilla, Cape Town (ZA); Deon Bezuidenhout, Cape Town (ZA)

(73) Assignee: Strait Access Technologies Holdings (PTY), Cape Town (ZA)

( * ) Notice: Subject to any disclaimer, the term of this patent is extended or adjusted under 35 U.S.C. 154(b) by 197 days.

(21) Appl. No.: 16/080,779

(22) PCT Filed: Mar. 1, 2017

(86) PCT No.: PCT/IB2017/051196
§ 371 (c)(1),
(2) Date: Aug. 29, 2018

(87) PCT Pub. No.: WO2017/149471
PCT Pub. Date: Sep. 8, 2017

(65) Prior Publication Data
US 2019/0053928 A1 Feb. 21, 2019

(30) Foreign Application Priority Data
Mar. 1, 2016 (GB) ...................... 1603580

(51) Int. Cl.
*A61F 2/958* (2013.01)
*A61F 2/24* (2006.01)
*A61M 25/10* (2013.01)

(52) U.S. Cl.
CPC ............ *A61F 2/958* (2013.01); *A61F 2/2433* (2013.01); *A61M 25/1002* (2013.01);
(Continued)

(58) Field of Classification Search
CPC ... A61F 2/958; A61F 2/2433; A61M 25/1002; A61M 25/0054
See application file for complete search history.

(56) References Cited

U.S. PATENT DOCUMENTS 4,243,040 A  1/1981  Beecher
4,318,410 A * 3/1982  Chin ................... A61M 25/104
                                                    606/194

(Continued)

FOREIGN PATENT DOCUMENTS

GB       1511557        5/1978
GB       2501490        10/2013
WO   2005007219 A2     1/2005

OTHER PUBLICATIONS

Parker, Matthew, Combined Search and Examination Report under Sections 17 and 18(3) from priority application GB 1603580.0; dated Jul. 27, 2016, pp. 1-5, Intellectual Property Office of the United Kingdom.

*Primary Examiner* — Tuan V Nguyen
(74) *Attorney, Agent, or Firm* — Ballard Spahr LLP (57) ABSTRACT

The invention provides an inflatable insertion device capable of being percutaneously introduced into a patient's body. The insertion device comprises an inflatable element having a distal end and a proximal end and which is operable between a collapsed condition and an inflated condition by introducing an inflating fluid therein. An elongate member (Continued)

extends internally of the inflatable element from its distal end. The internal member is capable of being withdrawn towards the proximal end of the inflatable element to result in the distal end of the element being withdrawn towards the proximal end internally of the element. The invention further provides a locating device comprising a catheter having a catheter tube fitted with one or more inflatable insertion devices at a distal end thereof.

13 Claims, 8 Drawing Sheets

(52) U.S. Cl.
CPC . *A61F 2220/005* (2013.01); *A61F 2220/0058* (2013.01); *A61F 2220/0075* (2013.01); *A61F 2230/0013* (2013.01); *A61F 2230/0041* (2013.01); *A61F 2230/0091* (2013.01); *A61F 2230/0097* (2013.01); *A61F 2240/00* (2013.01); *A61F 2250/0039* (2013.01); *A61M 2025/1052* (2013.01); *A61M 2025/1065* (2013.01); *A61M 2025/1068* (2013.01)

(56) References Cited

U.S. PATENT DOCUMENTS

| | | | | |
|---|---|---|---|---|
| 5,690,642 | A * | 11/1997 | Osborne | A61F 2/958 604/103.04 |
| 6,039,721 | A * | 3/2000 | Johnson | A61F 2/958 604/103 |
| 7,201,770 | B2 | 4/2007 | Johnson et al. | |
| 9,066,799 | B2 | 6/2015 | Seguin et al. | |
| 2004/0116963 | A1 * | 6/2004 | Lattouf | A61B 17/0401 606/224 |
| 2005/0090846 | A1 | 4/2005 | Pedersen et al. | |
| 2006/0086701 | A1 * | 4/2006 | Perreault | B29C 65/1664 219/121.64 |
| 2006/0122633 | A1 * | 6/2006 | To | A61B 17/0682 606/139 |
| 2008/0045928 | A1 * | 2/2008 | Simpson | A61M 25/10 604/525 |
| 2008/0157444 | A1 * | 7/2008 | Melsheimer | A61M 25/1027 264/514 |
| 2009/0018501 | A1 | 1/2009 | Yribarren et al. | |
| 2010/0125244 | A1 * | 5/2010 | McAndrew | A61M 25/10 604/98.01 |
| 2013/0046332 | A1 * | 2/2013 | Jones | A61M 25/1002 606/200 |
| 2015/0066068 | A1 | 3/2015 | Hirszowicz et al. | |
| 2015/0141917 | A1 * | 5/2015 | Tilson | A61F 2/958 604/103.07 |

* cited by examiner

INFLATABLE INSERTION DEVICE FOR PERCUTANEOUS INSERTION

CROSS REFERENCE TO RELATED APPLICATIONS

This application is a U.S. National Phase Application of International Patent Application No. PCT/IB2017/051196, filed Mar. 1, 2017, which claims priority to Great Britain Patent Application No. 1603580.0, filed Mar. 1, 2016, both of which are herein incorporated by reference in their entireties.

FIELD OF THE INVENTION

This invention relates to medical devices and, more particularly, it relates to inflatable percutaneously insertable medical devices.

BACKGROUND TO THE INVENTION

Inflatable medical devices are becoming increasingly popular since they enable a device to be percutaneously inserted into a patient's body and then inflated to their required size at the particular target location. The inflatable devices generally comprise one or more elongate flexible tubes that may have a specific pre-set shape which the device adopts once inflated by means of an inflation fluid. These devices may simply comprise elongate tubes which radially expand when inflated.

These inflatable devices may be used to deploy and/or position a prosthetic stent or valve which can be introduced percutaneously into the body. Inflatable devices may be used to position an inserted prosthetic by expanding externally to the prosthetic and deflated and retracted when the prosthetic is in position. Inflatable devices may also be used to expand a prosthetic from its compressed condition to its expanded condition in which the stent or valve remains in the body to fulfil its function. However, more complex inflatable devices having a spiralled or helical shape when inflated are also disclosed in the prior art. Such complex shapes are generally designed to be non-occlusive and thus permit normal blood flow during the procedure.

The use of inflatable medical devices has significantly increased in the field of heart valve replacements since they enable the procedure to be performed percutaneously or minimally invasively. In the case of transcatheter heart valve replacements in which a damaged or improperly functioning native heart valve is replaced by a replacement valve, instead of removing the native valve, the replacement valve is wedged into the native valve's place. Once in place, the replacement valve pushes the native valve leaflets out of the way and the leaflets of the replacement valve take over the job of regulating the blood flow. Since the replacement valve is intended to completely replace the native valve once in place, the success of the procedure is directly related to the correct positioning of the replacement valve with reference to the native valve.

Current procedures generally rely on expensive imaging systems such as echocardiography or fluoroscopy to enable the clinician to effectively locate and position the valve deployment device relative to the native valve. This method of positioning a replacement valve is thus substantially operator dependent and often causes replacement valves to be incorrectly placed and/or positioned, even in optimal conditions. The incorrect placement or positioning of the replacement valve can result in the embolization or incompetence of the replacement valve with obvious adverse effects.

In addition, in the case of balloon expandable replacement valves, with the balloon typically being occlusive in nature, rapid ventricular pacing is performed prior to valve deployment so as to reduce cardiac output. Although reduction in the cardiac output prevents the replacement valve from embolising during deployment and has the advantage of stabilising the valve annulus, it requires additional intervention in an already compromised heart and should thus be avoided if possible.

In order to avoid stressing of the compromised heart through rapid ventricular pacing, self-deploying valves which do not require occlusive deployment systems such as an inflatable device or balloon catheter have been proposed. Prior U.S. Pat. No. 8,303,653 proposes such a self-deploying valve which makes use of one or more locating arms that extend from the stent and that are capable of hooking behind the leaflets of the native valve so as to enable the valve to be correctly positioned relative to the native valve. The arms enable the clinician to determine the correct position of the replacement valve using tactile feedback and thus substantially negate the necessity for imaging. Nevertheless, since the arms are attached to the replacement valve, they must remain even after deployment of the valve.

Irrespective of the type of replacement valve used, during deployment thereof the generally diseased native valve anatomy, which may comprise calcified, thickened and/or fibrous tissue, is forcefully expanded against the vessel or cavity walls in which it is located. Any structure that is located between the device and the cavity walls or between the valve anatomy and the cavity walls may thus be sandwiched therebetween. Attempts to remove such trapped structures may cause direct harm to the patient or cause valve migration, dislodging of calcium, or embolization which may be fatal to the patient.

The above problems associated with elements or structures that may be sandwiched between a vessel or cavity wall and the device to be implanted may of course also apply to any other medical procedure. For example, where inflatable balloons are used and these are pinched between the vessel wall and another element or device it may be very difficult or almost impossible to remove the balloon once deflated without causing it to tear or to inadvertently move the element or device which has caused the pinching to occur.

The preceding discussion of the background to the invention is intended only to facilitate an understanding of the present invention. It should be appreciated that the discussion is not an acknowledgment or admission that any of the material referred to was part of the common general knowledge in the art as at the priority date of the application.

SUMMARY OF THE INVENTION

In accordance with the invention there is provided an inflatable insertion device capable of being percutaneously introduced into a patient's body, the device comprising an inflatable element having a distal end and a proximal end and being operable between a collapsed condition and an inflated condition, characterised in that an elongate member extends internally of the inflatable element from the distal end thereof and which is capable of being withdrawn towards the proximal end of the element to result in the distal end being withdrawn towards the proximal end internally of the element and wherein the inflatable element is a non-compliant inflatable element and pre-set to a desired shape so as to adopt the pre-set shape when inflated.

Further features provide for the elongate member to be more flexible than the inflatable element when in its desired shape, such that the inflatable element retains its pre-set desired shape during withdrawal of the distal end to the proximal end.

Further features provide for the inflatable insertion device to include an inflation tube at or near the proximal end of the of the inflatable element through which inflating fluid may be introduced into the inflatable element; for the inflatable element to be in the form of an elongate tube; for the inflatable element and the inflation tube to be integrally manufactured; for the inflatable element to be capable of resisting pressures within the range from about 5 bar up to about 50 bar, preferably from about 8 bar up to about 30 bar; for the elongate tube to have a diameter, by way of non-limiting example, of the order of 0.8 to 8 millimetres, preferably about 5 millimetres; for the elongate tube to optionally have a varying diameter along its length so as to provide for an inflatable element having a beaded shape when inflated; for the inflatable element to be pre-set to a desired shape so as to adopt the pre-set shape when inflated; and for the pre-set shape to include any suitable shape including straight, bent, spiral, semi-circle or other suitable shape.

Further features provide for the elongate member to be flexible; for the elongate member to extend through the proximal end of the inflatable element and preferably though the inflation tube; for the elongate member to be capable of withdrawing the distal end of the inflatable element through the proximal end thereof; for the elongate member and the inflatable element to be manufactured integrally; alternatively, for the elongate member to be manufactured from any suitable material including natural materials such as linen, hemp or silk, or from synthetic materials such as nylon, Kevlar®, vectran, prolene or the like; and for the elongate member to be secured to the distal end of the inflatable tube by means of an adhesive, ultrasonic welding, thermal bonding, by means of a knot about a portion of the inflatable element material and other suitable attachment procedures.

The invention extends to a locating device comprising a catheter having a catheter tube fitted at a distal end thereof with one or more inflatable insertion devices as defined above and having at least one connection point at a proximal end of the catheter tube whereby inflating fluid can be conveyed to the one or more inflatable insertion devices by way of a lumen associated with the catheter tube.

Further features provide for the locating device to have multiple inflatable insertion devices, preferably three, fitted at the distal end of the catheter tube evenly spaced about its circumference and orientated so that the distal ends of the inflatable elements are directed generally towards the proximal end of the catheter when in the inflated condition; and for each element to be curved along its length and configured to engage and seat of the bottom of a natural heart valve leaflet.

The invention extends to a method of locating and positioning a catheter relative to a desired location, the method comprising the steps of:

extending a distal end of a locating device percutaneously, the valve locating device comprising a catheter having a catheter tube fitted at a distal end thereof with one or more inflatable insertion devices, each inflatable insertion device comprising an inflatable element having a distal end and a proximal end and being operable between a collapsed condition and an inflated condition with an elongate member extending internally of the inflatable element from the distal end thereof and which is capable of being withdrawn towards the proximal end of the element to result in the distal end being withdrawn towards the proximal end internally of the element, the valve locating device having at least one connection point at a proximal end of the catheter tube whereby inflating fluid can be conveyed to the one or more inflatable insertion devices by way of a lumen associated with the catheter tube;

conveying inflating fluid to the inflatable element of each inflatable insertion device via the lumen associated with the catheter tube so as to cause the inflatable elements to inflate;

retracting the catheter so as to cause the inflatable elements to engage and seat in desired positions; and selectively shortening the length of one or more inflatable elements by withdrawing the elongate member that extends from the distal end of the inflatable element so as to cause the distal end of the inflatable element to withdraw towards its proximal end so as to move the catheter relative to the desired location.

Further features provide for the method to include the steps of, when the desired location is an aortic valve, extending the distal end of the locating device percutaneously, extends the locating device through the aortic valve from the left ventricle through the aortic valve and into the aortic root; and selectively shortening the length of one or more inflatable elements is carried out so as to move the catheter relative to the aortic annulus.

Inflatable elements may be manufactured from any suitable material including polyethylene terephthalate (PET) or other suitable material. If the inflatable elements are manufactured using heat shrink materials by a method as defined above, then suitable materials may be selected from polyethylene terephthalate (PET) in particular, polyolefin, polytetrafluoroethylene (PTFE), fluorinated ethylene propylene (FEP), perfluoroalkoxy (PFA), ethylene tetrafluoroethylene (ETFE), polyester, polyether ether ketone (PEEK), polyvinyl chloride (PVC) or even combination thereof materials.

Inflatable elements manufactured using other methods may be made of materials selected from silicones, latex, Kraton, thermoplastic elastomers such as styrene-ethylene/butylene-styrene block copolymers (SEBS), (SEBS)-based thermoplastic elastomers, polysiloxane modified SEBS and families of SEBS, PVC, cross-linked polyolefins such as polyethylene, and many different polyurethanes. Preferred materials are those known as semi-compliant or non-compliant (inelastic) materials which include polyamides (e.g. nylons), polyesters (for example and preferably PET), thermoplastic polyamides, and polyphenenylene sulphides.

In order that the invention may be more fully understood various embodiments of the different aspects of the invention will now be described with reference to the accompanying drawings.

DETAILED DESCRIPTION WITH REFERENCE TO THE DRAWINGS

Figure 1:
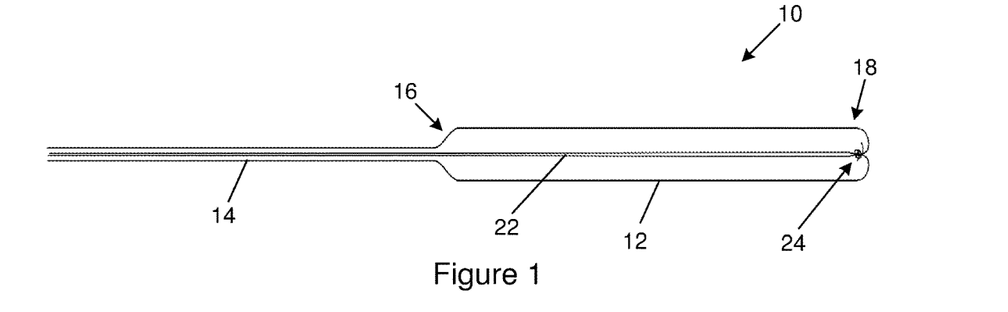
FIG. 1 is a longitudinal sectional view of one embodiment of an inflatable insertion device in accordance with the invention, in which the inflation tube and inflatable element are integrally manufactured.
Figure 2:
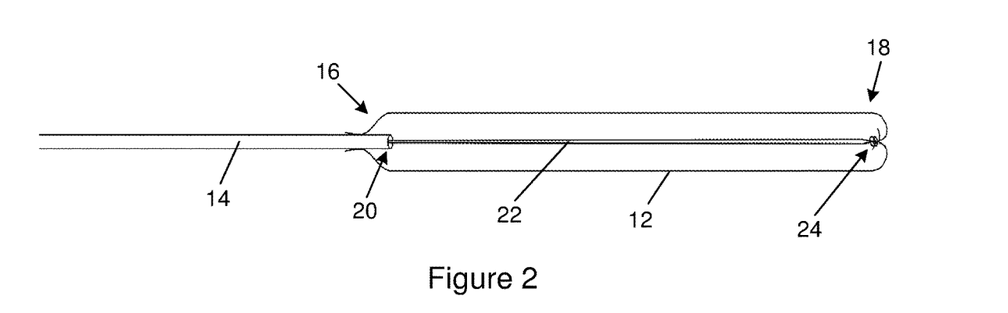
FIG. 2 is a partial longitudinal sectional view of one embodiment of an inflatable insertion device in accordance with the invention, in which the inflation tube and inflatable element are manufactured separately from one another and the inflatable element is then secured over the distal end of the inflatable tube.
Figure 3A:
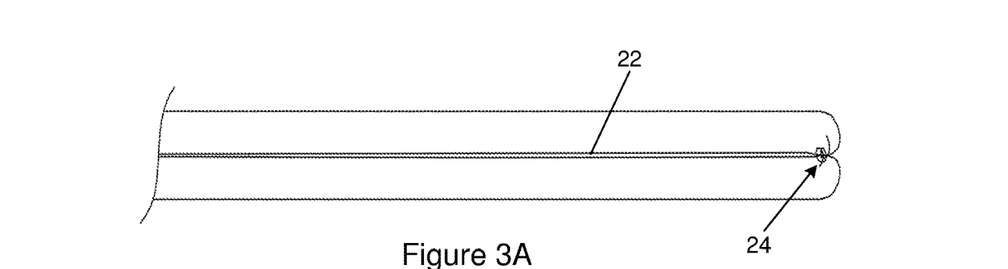
FIGS. 3A to 3C illustrate various embodiments of inflatable elements having different elongate members extending internally thereof from the distal end of the inflatable element.
Figure 3B:
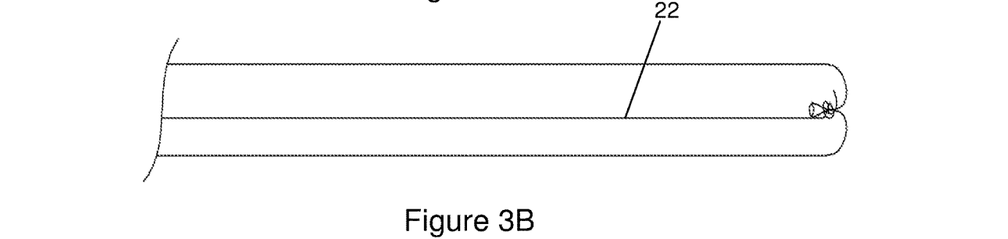
Figure 3C:
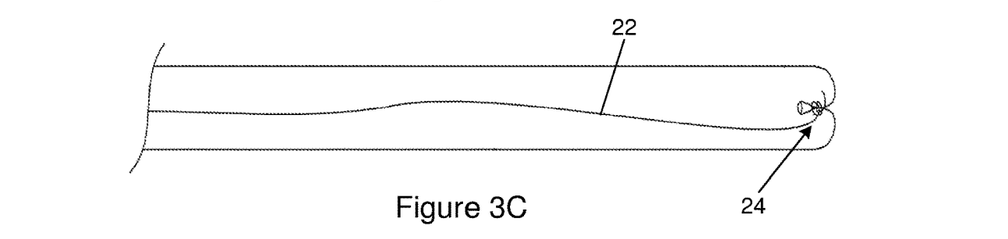

Referring firstly to FIGS. 1 to 3 of the drawings, an inflatable insertion device (10) comprises an inflatable element (12) having an inflation tube (14) at its proximal end (16) and which is closed off at its distal end (18). Inflating fluid may be introduced into the inflatable element (12) through the inflation tube (14) to thereby inflate the element (12) from a collapsed condition to an inflated condition. It will be appreciated that the inflatable insertion device may also be inflated when in an invaginated state, as will be described in more detail below. In the collapsed condition, the inflatable element (12) is collapsed and preferably folded either systematically or randomly to permit the device (10) to be inserted percutaneously into a vessel or other hollow organ of a patient, as will be described in more detail further below. In the inflated condition on the other hand, the inflatable element (12) assumes any desired pre-set shape suitable for the procedure to be performed. The pre-set shape of the inflatable element (12) may include any suitable shape required for the particular procedure including straight, bent, spiral, semi-circle or the like.

Figure 5:
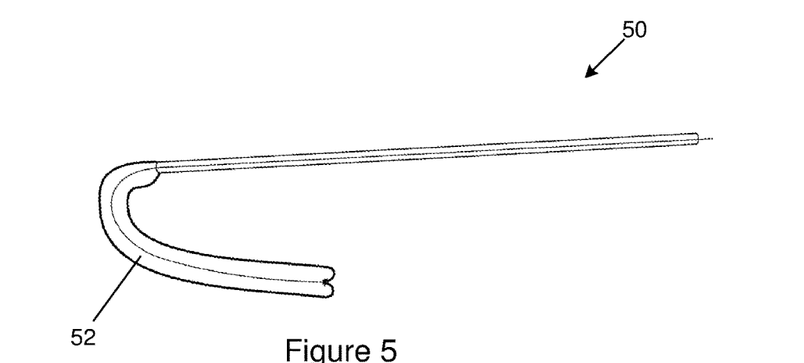
FIGS. 5 to 7 show side views of embodiments of inflatable insertion devices in which the inflatable element of each embodiment has a different pre-set shape.

The inflatable insertion device (10) disclosed may be used for a variety of procedures including as a device for the deployment of prosthetic heart valves, for the deployment of stents in calcified blood vessels, to occlude a blood vessel so as to prevent blood flow to a particular region in the body or it may form part of other devices. For example, and as will be described in more detail further below, an inflatable insertion device according to the invention may have a pre-set bent or hooked shape, as shown in FIG. 5, in which case it may be used hook or temporarily secure a catheter or other device at a target location so as to prevent the devices accidental removal during the procedure. Alternatively, the hooked or bent shape of the device may be used to locate a particular feature or part of an organ by engaging therewith and providing the clinician with tactile feedback indicating that the feature has been successfully located. This may be of particular relevance during heart valve replacement procedures, as will be described in more detail further below.

In the embodiment illustrated, the inflatable element (12) is in the form of an elongate tube but any other suitable shaped element may also be used. Since the inflatable insertion device (10) is percutaneously insertable, it has a diameter of about 0.8 to about 8 millimetres, depending on the application thereof. As a general rule the inflatable element will have a rather thin wall that may be in the order of 10 to 50 μm, preferably from about 12 to 40 μm, in the instance where a suitable heat shrink material is used, as will be described in more detail below. In addition, the material of the inflatable element (12) is selected so that the element is capable of resisting pressures in the range of about 5 to 50 bar, preferably about 10 to 15 bar.

In the embodiment illustrated in FIG. 1, the inflatable element (12) and the inflation tube (14) are integrally formed. However, it will of course be appreciated that the inflation tube (14) and the inflatable element (12) may be manufactured separately with the proximal end (16) of the inflatable element (12) then being tightly secured over the distal end (20) of the inflation tube (14), as illustrated in FIG. 2. In such a case, the inflatable element (12) is preferably secured over the distal end (20) of the inflation tube (14) by means of and adhesive, ultrasonic welding or thermal bonding so as to ensure a tight seal therebetween and prevent the inflatable element (12) from dislodging from the tube (14) during inflation.

Figure 8:
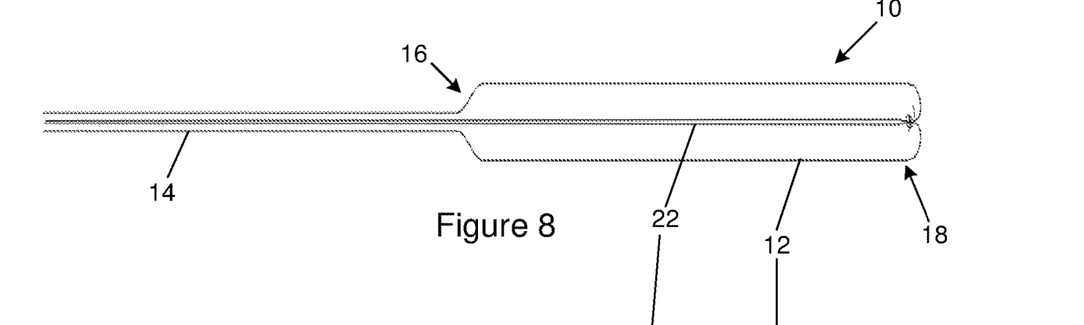
FIGS. 8 to 9 show how the distal end of the inflatable element is withdrawn towards the proximal end thereof through withdrawal of the elongate member.
Figure 9:
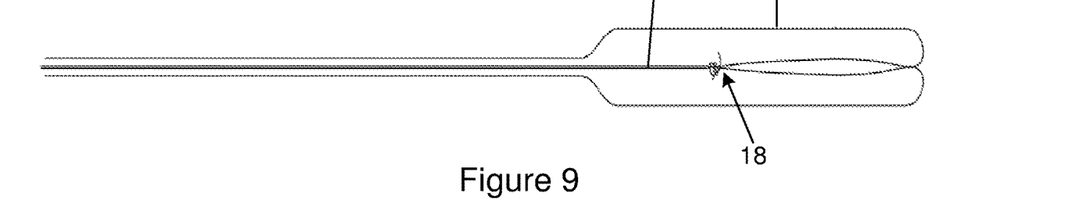

The inflatable insertion device (10) further includes an elongate member (22) that extends internally of the inflatable element (12) from its distal end (18) and through the proximal end (16) of the inflatable element (12). In the embodiments illustrated in FIGS. 1 and 2, the elongate member (22) extends through the proximal end (16) of the inflatable element (12) and into the inflation tube (14). Withdrawing of elongate member (22) through the proximal end (16) of the inflatable element (12) results in the distal end (18) of the element (12) being withdrawn towards the proximal end (16), as is best illustrated in FIGS. 8 and 9. The distal end (18) is withdrawn internally of the element (12) and may eventually be withdrawn through the proximal end (16) of the element (12). By enabling the inflatable element (12) to be withdrawn into itself, or in an invaginating manner, any shear forces that may develop on the outside surfaces of the element (12) through removal thereof, will be substantially eliminated. It will be appreciated that the removal or substantial elimination of shear forces may be of particular relevance in situations where the device, in this case the inflatable element, may be pinched between surfaces and sheer forces should not be transferred to the pinching structures. For example, and as will be described by way of example further below, during deployment of a prosthetic heart valve, the deployed valve may pinch a device or portion thereof between its outer surface and the inner surface of the organ in which the valve is deployed. In such a case, none or as little as possible sheer forces should be exerted onto the valve since these may move or cause embolization of the valve or dislodge calcium that may have deposited at the valve location.

It will of course be appreciated that in order to facilitate the withdrawal of the distal end (16) of the inflatable element (12), the inflatable element (12) should be slightly deflated from its fully inflated condition so as to reduce the pressure within the element (12) thereby reducing the force required to withdraw the distal end (18) toward the proximal end (16). This will be described in more detail further below, but should be noted that the inflatable element is not completely deflated but remains pressurized such that the pre-set, desired shape thereof is retained during withdrawal.

In the embodiments illustrated in FIGS. 1, 2 and 3A, the elongate member (22) is integrally formed with the inflatable element (12). A method of manufacturing such an inflatable insertion device (10) will be described in more detail further below. Nevertheless, and as illustrated in FIGS. 3B and 3C, the elongate member (22) may also be a manufactured separately and then simply secured to the distal end (18) of the inflatable element (12). In such a case, the elongate member (22) may be in the form of a string manufactured from any suitable material including natural materials such as linen, hemp or silk, or synthetic materials such as nylon, Kevlar®, vectran, prolene or the like. In addition, if manufactured separately, the elongate member (22) may be secured to the distal end (18) of the inflatable element (12) by means of knotting the member (22) about a portion of the inflatable element (12), an adhesive, ultrasonic welding, thermal bonding or the suitable attachment methods. In the embodiment illustrated in FIG. 3C, the elongate member (22) is manufactured from an elastic material which permits the member (22) to stretch during inflating of the inflatable element (12) and causes the member (22) to retract if the inflatable member (12) is somewhat deflated. In such a way, the elasticity of the member (22) can assist in withdrawing the distal end (18) of the inflatable member (12) toward the proximal end (16) thereof simply through deflation of the element (12).

Also, and this is particularly relevant for the embodiments illustrated in FIGS. 1, 2 and 3A in which the elongate member (22) is manufactured integrally with the inflatable element (12), a growth prevention knot (24) is provided near the point where the elongate member (22) extends from the distal end (18) of the inflatable element (12). The growth prevention knot (24) ensures that the elongate member (22) does not separate along its length through inflation of the element (12) and consequent increasing in length or distortion in shape of the inflatable element during inflation thereof. Of course, in the event where the elongate member (22) is secured to the distal end (18) of the inflatable element (12) by means of knotting the member (22) about a portion of the inflatable element (12), as best illustrated in FIGS. 3B and 3C, then the knot securing the member will also act as the growth prevention knot (24). On the other hand, where the elongate member (22) is secured to the distal end by means of an adhesive or thermal bonding, then a growth prevention knot may not be required.

Figure 4:
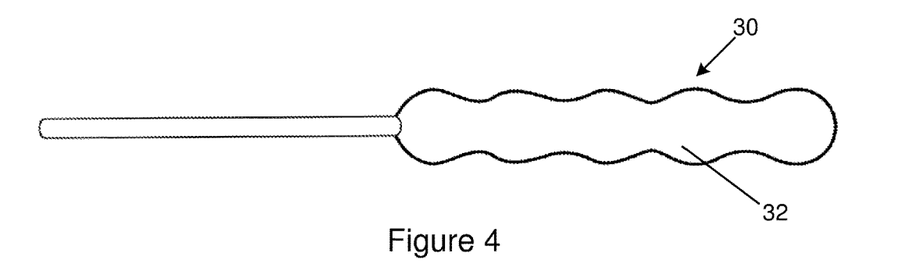
FIG. 4 is a side view of one embodiment of an inflatable insertion device in accordance with the invention, in which the inflatable element has a varying diameter so as to provide for a beaded shape when in the inflated condition.

It is also envisioned to provide for inflatable insertion devices (30) in which the inflatable element (32) has a varying diameter along its length so as to provide for an inflatable element (32) having a beaded shape when in the inflated condition, as best illustrated in FIG. 4. The beaded shape of the inflatable element (32) may enhance perfusion around the element (32).

Figure 6:
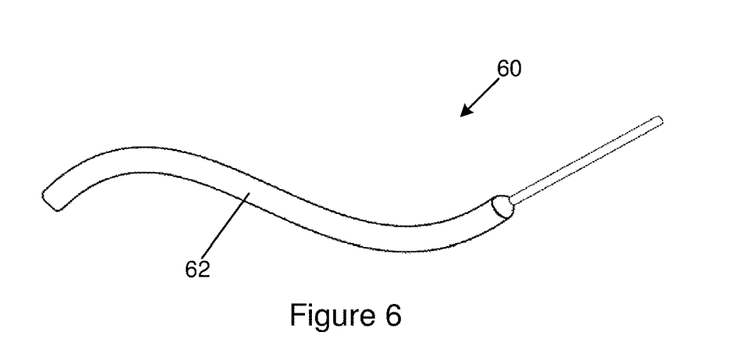
Figure 7:
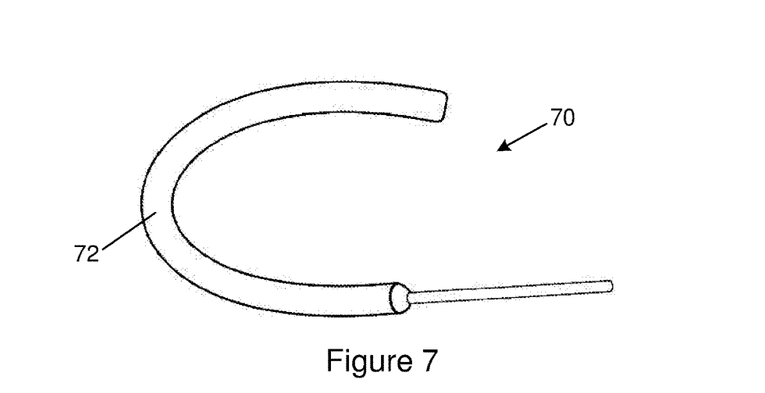

In addition, and as illustrated in FIGS. 5 to 7, during manufacture of an inflatable insertion device (50, 60, 70), the inflatable element (52, 62, 72) may be pre-set to a desired shape. When the inflatable element (52, 62, 72) is then later inflated, the element (52, 62, 72) will adopt the pre-set shape. Thus, in the embodiment shown in FIG. 5, the inflatable element (52) may have a hook-like shape when inflated. This may then be used to hook or temporarily secure the device at a target location which may, as will be explained in more detail further below, be of particular relevance during heart replacement procedures. However, the pre-set shape of the inflatable element may include any suitable shape including straight, bent, spiral, semi-circle or the like.

The inflatable element may be a non-compliant inflatable element as is known in the art. Non-compliant inflatable elements show a relatively small change in volume with incremental increases in pressure when inflated, particularly when compared to semi-compliant inflatable elements. This may assist in the inflatable element retaining its desired pre-set shape when inflated. It should be noted that non-compliant inflatable elements may still be partially flexible. Typically, such non-compliant inflatable elements are made using thin, sheet-like material which is flexible but not elastic to any significant extent.

FIG. 8 illustrates the inflatable insertion device (10) of FIG. 1 with the elongate member (22) extending from the distal end (18) of the inflatable element (12) and out of the proximal end of the inflation tube (14). Withdrawal of the elongate member (22) causes the distal end (18) of the inflatable element (12) to be withdrawn, internally of the element (12), as shown in FIG. 9. In this way the inflatable element (12) can be withdrawn entirely into the inflation tube (14), provided of course the inflatable element (12) is sufficiently deflated since the tube (14) has a smaller diameter than the inflated element (12). It should be noted that the inflatable element will remain inflated during withdrawal thereof. The inflatable element thus retains its structure during withdrawal.

Figure 10A:
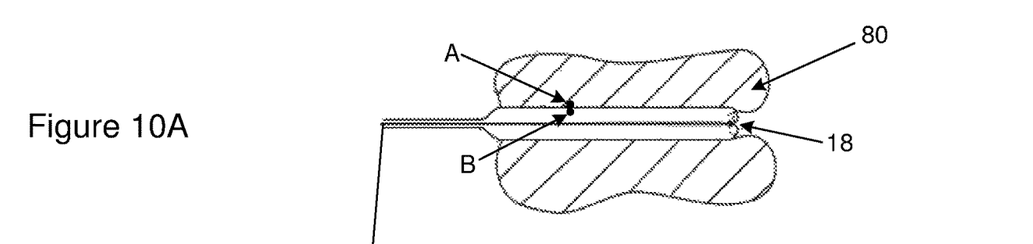
FIGS. 10A to 10C schematically show how the inflatable insertion device illustrated in FIGS. 8 and 9 can be withdrawn from a vessel or other hollow organ of a patient.

In this regard, FIGS. 10A to 10O schematically show how the inflatable insertion device (10) illustrated in FIGS. 8 and 9 can be withdrawn from a vessel or other hollow organ (80) of a patient. As the elongate member (22) is withdrawn through the proximal end of the inflation tube (14), the distal end (18) of the inflatable element (12) is withdrawn towards the proximal end (16) of the inflatable element internally thereof whilst the inflatable element is pressurized and in its pre-set shape. Withdrawal of the distal end (18) causes the inflatable element (12) to decrease in length, whilst maintaining its pre-set desired shape, until the inflatable element is eventually completely removed from the vessel or other hollow organ (80). Removal of the inflatable element (12) by withdrawing its external surfaces through and into itself permits the external shear forces acting onto the inflatable element to be eliminated.

Shear or frictional forces are forces that act in the opposite direction of an applied force and, in a dynamic case, in the opposite direction of relative movement. A relative frictional force arises when there is a force exerted to move one surface in relative motion to another whilst the two surfaces experience a force contact or normal force. In this way, friction can be seen as the force preventing relative motion between two surfaces in contact.

Figure 10B:
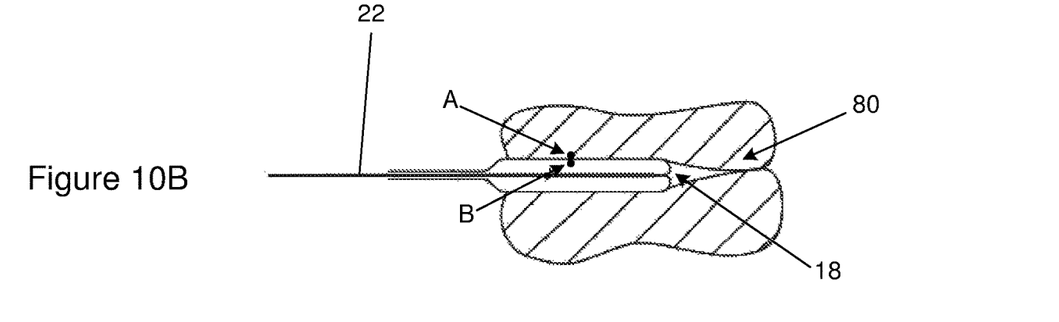
Figure 10C:
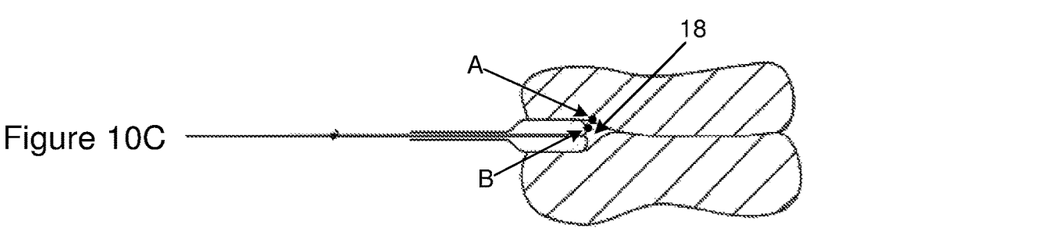

During withdrawal of the elongate element, the inflatable element invaginates within itself. The invaginating within itself process does not create a motion or acting force between point A and B in FIG. 10A, although a normal force is retained. Since there is no acting force between point A and B, there is no reactive frictional force to oppose it. As the distal end of the inflatable element is further withdrawn, as shown in FIG. 10C, eventually point B will begin to experience forces inducing relative motion from point A. However, since point B essentially loses contact to point A at the exact moment when the relative motion is induced, the normal force between the two points is eliminated. Thus, during the period of relative motion, no normal force and therefore no frictional force is present, resulting in the absence of shear stresses between point A and B.

It will be appreciated that the elimination of shear stresses between point A and B as described with reference to FIGS. 10A to 10C applies to the entire outer surface of an inflatable element during withdrawal thereof by invaginating the element within itself. Removal of an inflatable element thus does not result in relative movement between the outside surfaces of an inflatable element and a surrounding structure, be it another device or the walls of an organ or other hollow structure. By substantially eliminating the development of shear forces on the outside surface of the inflatable element, the element may be easily removed from its target location, even when pinched, without causing the pinching structures to be moved or otherwise disturbed. This will be of particular relevance where an inflatable insertion device is used to locate a native valve and position a catheter relative thereto for deployment of a prosthetic valve. This will be described in more detail below with reference to FIGS. 17 to 19.

The inflatable elements used for the inflatable insertion device are preferably manufactured from polyethylene terephthalate (PET), but any other suitable material may be used. For example, if the inflatable elements are manufactured using heat shrink materials, then the material may be selected from polyethylene terephthalate (PET), polyolefin, polytetrafluoroethylene (PTFE), fluorinated ethylene propylene (FEP), perfluoroalkoxy (PFA), ethylene tetrafluoroethylene (ETFE), polyester, polyether ether ketone (PEEK), polyvinyl chloride (PVC) or combinations thereof.

Figure 11:
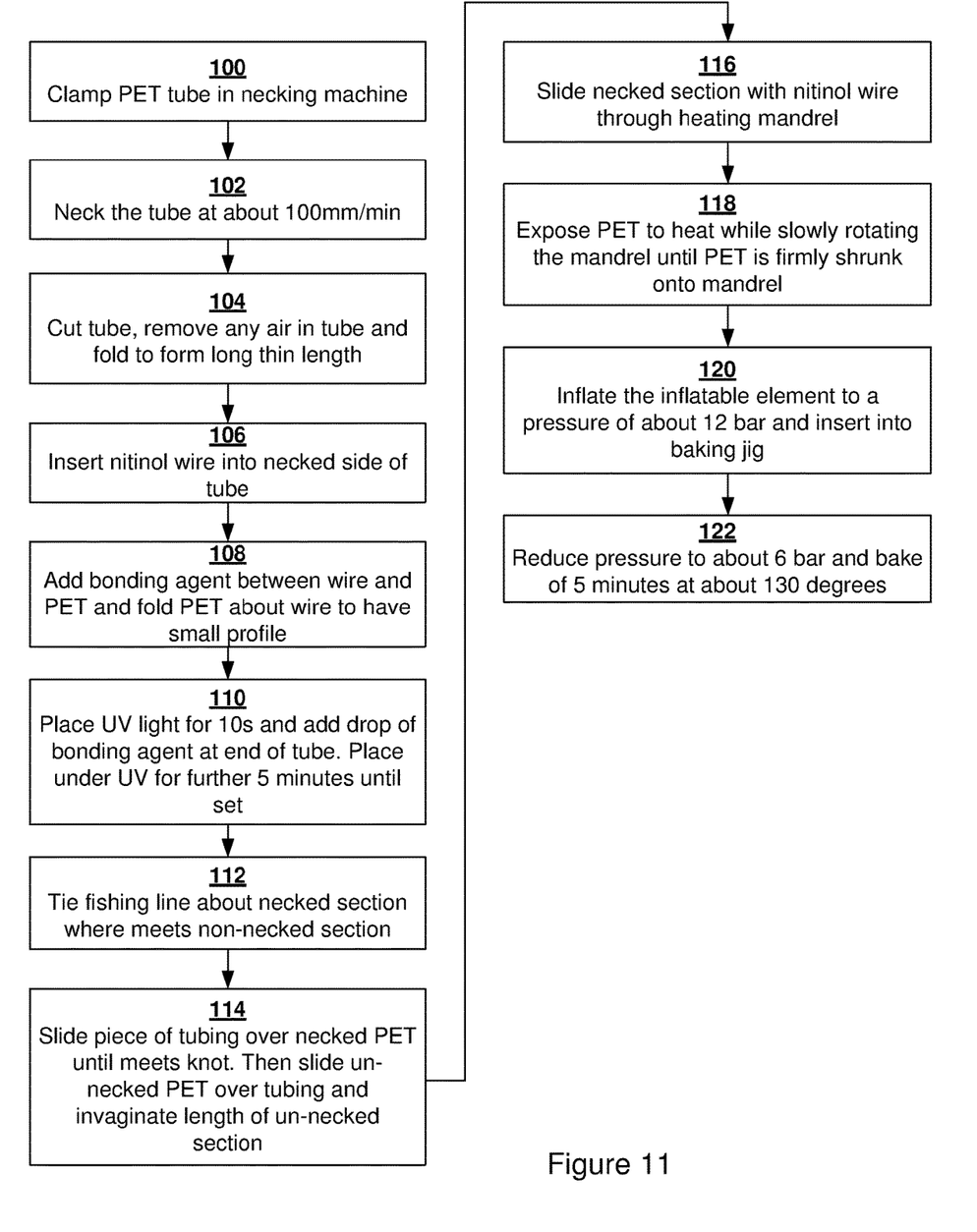
FIG. 11 is a flow diagram illustrating a method of manufacturing an inflatable insertion device illustrated in FIG. 1.

In order to manufacture an inflatable insertion device (10) as illustrated in FIG. 1, in which the elongate member (22) is integral with the inflatable element (12), the following method may be employed as illustrated in the flow diagram of FIG. 11. As a first step (100), tubes of a suitable heat shrink material, preferably PET, are selected and clamped into a necking machine with the length of tube between the clamps being about 180 mm, but the length may vary depending on application of the inflatable insertion device (10).

At a next step (102), the tube is necked at a speed of about 100 mm/min and the necking is stopped at a force of about 52N. Thereafter, at a next step (104), the necked side of the tube is cut approximately 10 mm into the necked section and any air within the tube is removed by simply running one's finger along the length to create a flat film that is then folded in half to form a long thin length.

At a next step (106), a piece of nitinol wire (140) having a diameter of about 0.6 mm and a length of about 1000 mm long is placed about 50 mm deep into the necked side of the tube. Thereafter, at a next step (108), preferably using a blunted needle, a bonding agent (142) such as 211 Dymax is injected between the nitinol wire and the PET. Any excess bonding agent is removed and the excess PET (144) is folded about the nitinol wire, in the direction of the arrow shown in FIG. 12, so as to ensure a small profile about the wire (140).

Figure 12:
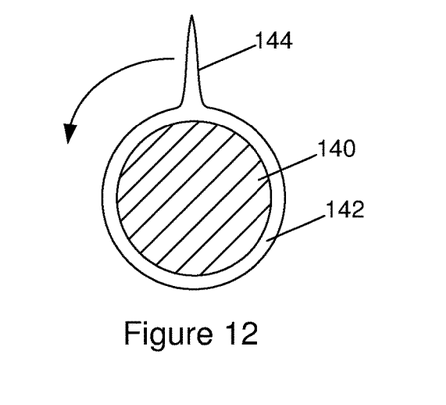
FIG. 12 is a cross-sectional view of a piece of nitinol wire surrounded by PET tubing illustrating a method of manufacturing an inflatable insertion device in accordance with the invention.

At a next step (110), the PET is placed under UV light for approximately 10 seconds after which a small drop of bonding agent is placed at the end of the tube to act as a lead in. The PET is then placed under the UV light for a further 5 minutes. Once the bonding agent has set, any air that may be in the necked section of the PET is again removed.

Figure 13A:
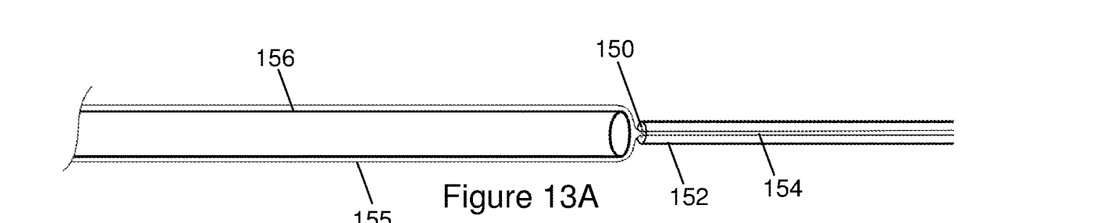
FIGS. 13A and 13B are two side views illustrating how the un-necked PET section is invaginated over the necked PET section.
Figure 13B:
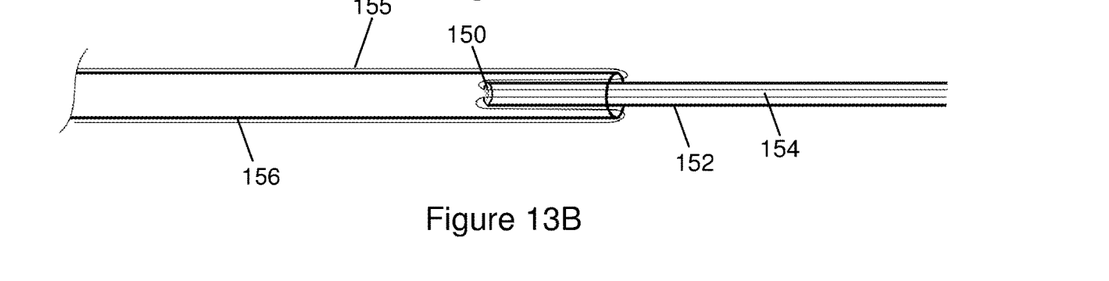

At a next step (112), a piece of rope or string, preferably monofilament dyneema, is tied about the necked section (154) where it meets the non-necked section (155) of the tube. The line is preferably knotted into a double death knot (150). At a next step (114) and as best illustrated in FIGS. 13A and 13B, a piece of tubing (152), preferably 2.6 mm nylon inflation line, is slid over the necked PET tube (154) up until it meets the knot (150). Thereafter, the non-necked end of the PET tube (155) is slid over an invaginating tube (156) again until it meets the knot (150). At a next step (115), the invaginating tube (156) is forced over the piece of nylon tubing (152) causing the un-necked PET section (155) to fold over itself and over the necked PET section.

Figure 14:
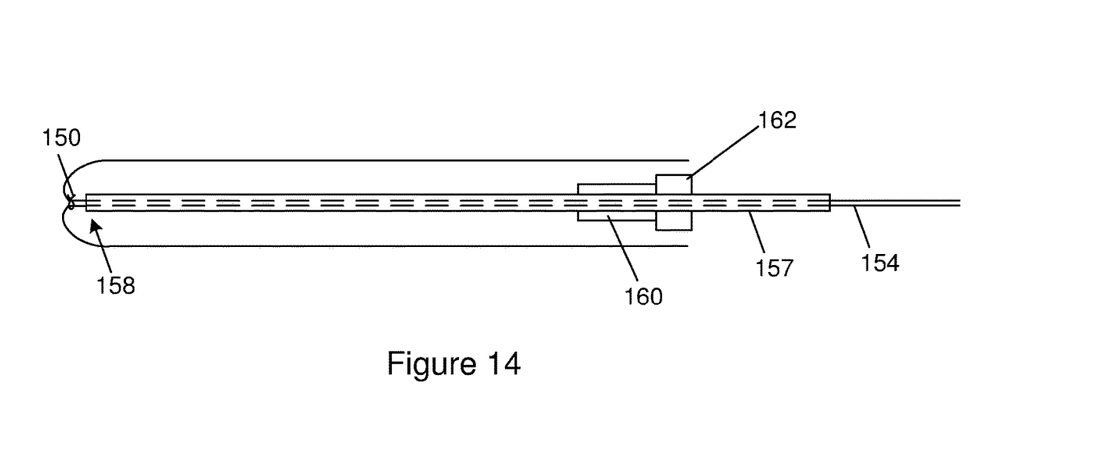
FIG. 14 is a side view of a heating mandrel to which a partially manufactured inflatable insertion device has been secured illustrating a further step in the method of manufacturing an inflatable insertion device shown in FIG. 11.

At a next step (116) and as shown in FIG. 14, the necked section of the PET tube (154) which includes the nitinol wire is slid through a heating mandrel (157) until the front end (158) of the mandrel (157) is adjacent the knot (150). Insulating silicon (160) is then slid over the front end of the PET and a radial tightening device (162) is placed over the end and against the insulating silicon (160). At a next step (118), a specific section of the un-necked PET is exposed to heat while slowly rotating the mandrel (157). It is important that the heat is not concentrated on a particular area for too long which may cause the PET to melt and create undesirable irregularities. The PET is exposed to the heat until the PET is firmly shrunk onto the mandrel (157).

Once this has been done, the inflatable insertion device (10) as shown in FIG. 1 has been manufactured.

Figure 15:
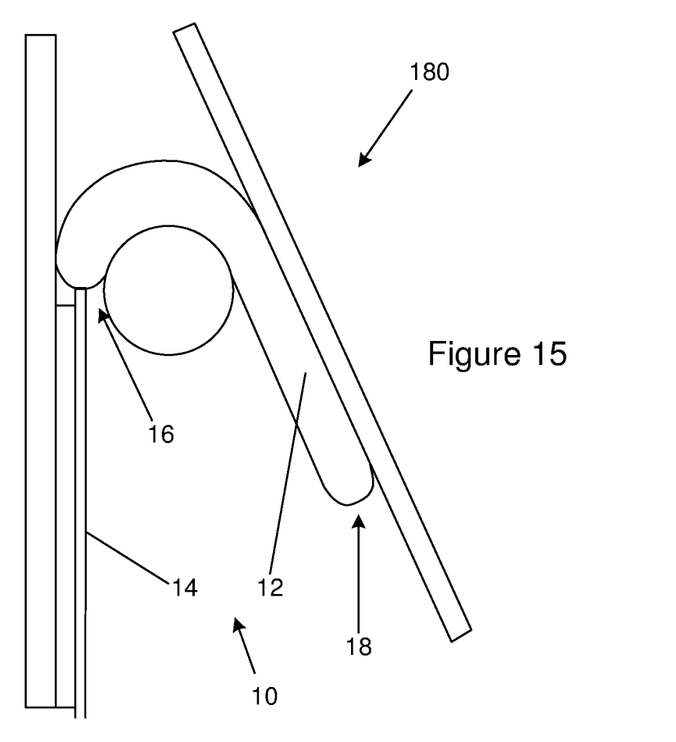
FIG. 15 is a schematic illustration of an embodiment of a baking jig setup which may be used to pre-set the inflatable element of an inflatable insertion device to a desired shape.
Figure 16:
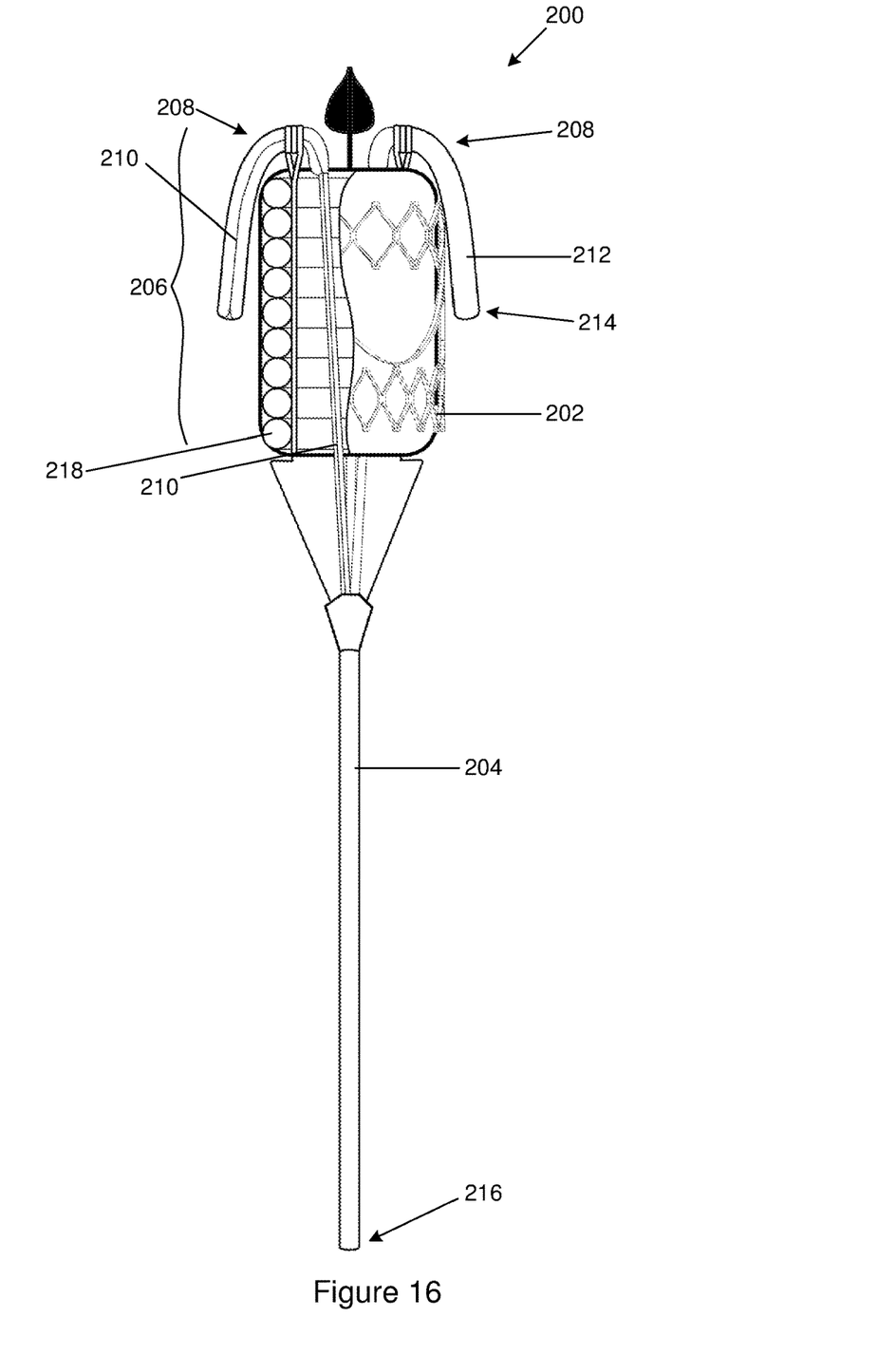
FIG. 16 is a partial longitudinal view of an embodiment of a valve locating device in accordance with the invention, in which the device includes a valve deployment device.

As described above, the inflatable elements (12) may be pre-set to a desired shape so as to adopt the pre-set shape once inflated. In order to pre-set the inflatable element (12) to a shape as shown in one of FIGS. 5 to 7, at a next step (120), the inflatable element (12) is inflated to a pressure of approximately 6 bar and the inflatable insertion device (10) is inserted into an appropriate baking jig (180). An embodiment of a baking jig (180) suitable for pre-setting the shape of the inflatable element (12) as shown in FIG. 5 is schematically illustrated in FIG. 15. At a next step (122), the pressure in the inflatable element (12) is reduced to approximately 6 bar and the device (10) is baked at about 130 degrees for approximately 5 minutes.

Of course, any other suitable method of manufacturing inflatable insertion devices in accordance with the invention may also be used. In addition, if other methods are used in which the material is not heat shrunk, then the materials used for the manufacture of the devices may be selected from silicones, latex, Kraton, thermoplastic elastomers such as styrene-ethylene/butylene-styrene block copolymers (SEBS), (SEBS)-based thermoplastic elastomers, polysiloxane modified SEBS and families of SEBS, PVC, crosslinked polyolefins such as polyethylene, and many different polyurethanes. Preferred materials are those known as semi-compliant or non-compliant (inelastic) materials which include polyamides (e.g. nylons), polyesters (for example and preferably PET), thermoplastic polyamides, and polyphenenylene sulphides.

FIGS. 16 to 19 illustrate an embodiment of a valve locating device (200) that is capable of deploying a prosthetic heart valve (202) at a target location within a patient. The device (200) comprises a catheter tube (204) that is fitted at its distal end (206) with three inflatable insertion devices (208), but any other suitable number may be used. The inflation tubes (210) of the insertion devices (208) extend the length of catheter tube (204) internally thereof to a point externally of the patient so as to enable the inflatable elements (212) to be inflated using an inflating fluid, preferably water but other suitable fluids may also be used. Instead of having the three individual inflation tubes (210) extend the entire length of the catheter tube (204), they may also meet at a central connection point and then connect to a single tube or lumen associated with the catheter tube (204) through which inflation fluid may be conveyed to the inflatable insertion devices (208). Nevertheless, it will be appreciated that where the inflation tubes (210) are kept separate, the inflatable insertion devices (208) can be inflated separately as and when required.

Figures 17, 18, 19:
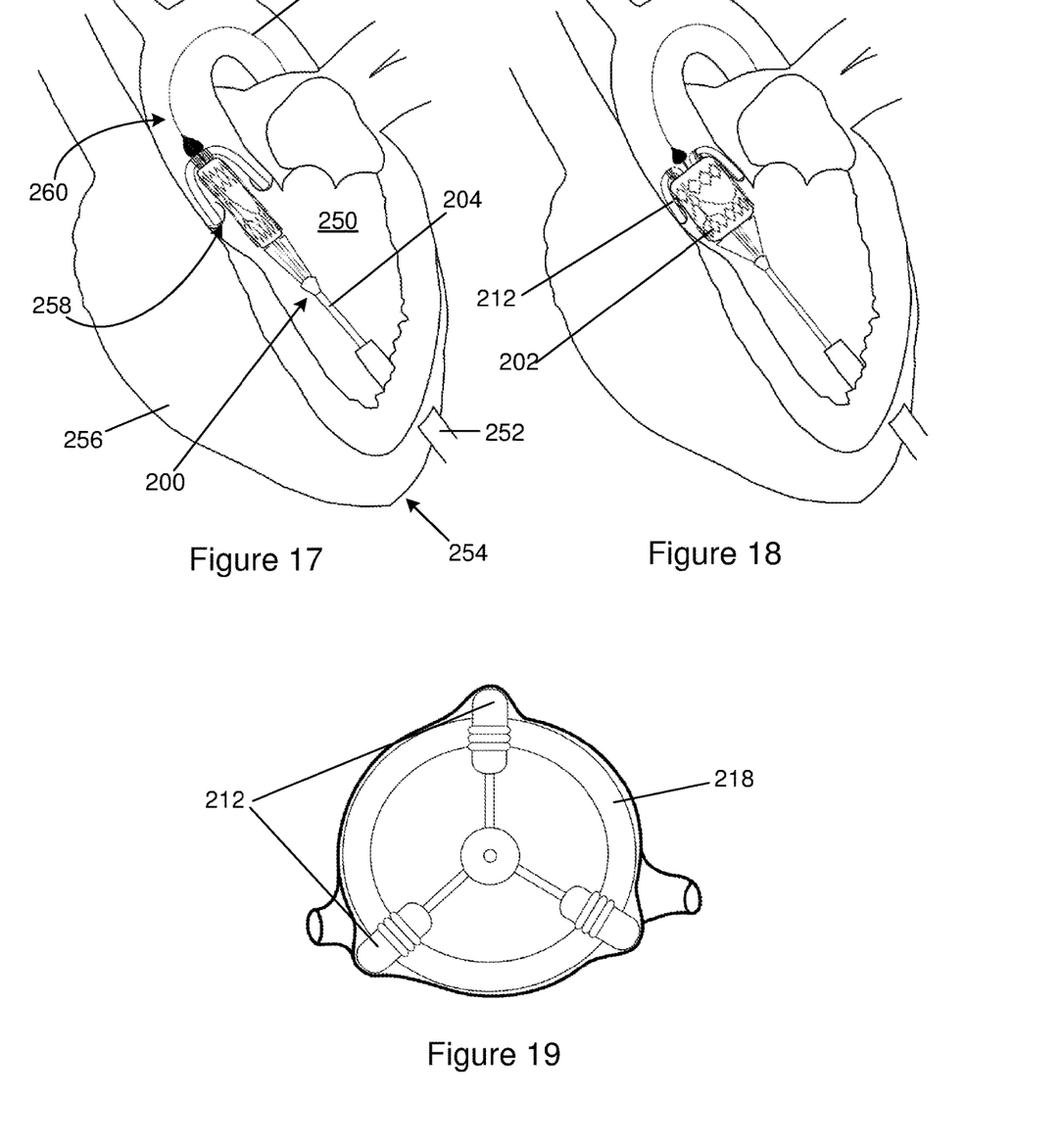
FIGS. 17 to 19 schematically show how the valve locating device of FIG. 16 may be used to locate an aortic valve and deploy a prosthetic valve therein.

The three inflatable insertion devices (208) are evenly spaced about the circumference of the catheter tube (204), as best illustrated in FIG. 19. In addition, the inflatable elements (212) of the inflatable insertion devices (208) have a pre-set shape similar to the embodiment shown in FIG. 5 and are orientated so that the distal ends (214) of the inflatable elements (212) are directed generally towards the proximal end (216) of the catheter tube (204) when inflated. However, it will of course be appreciated that the distal ends of the inflatable elements may also be directed towards the distal end of the catheter tube, for example where the device is used in a retrograde approach typically used for transfemoral procedures. The pre-set shape of the inflatable elements (212) which resembles a hook is configured to engage and seat of the bottom of a natural heart valve leaflet, as will be described in more detail further below.

The valve locating device (200) further includes a valve deployment device (218), in this embodiment in the form of an elongate balloon that extends in a generally spiral or helical path and which is capable of expanding the valve (202) as best illustrated in FIGS. 17 and 18. It will be appreciated that the valve deployment device (218) may also be a separate device from the valve locating device (200), with the earlier device (218) either being introduced once the natural heart valve has been successfully located by the valve locating device (200) and its catheter tube properly positioned with respect to the natural valve, or it may be a single device as disclosed in FIGS. 16 to 19.

In use and as illustrated in FIGS. 17 and 18, the device (200) is introduced into the left ventricle (250) via a transapical port (252) at the apex (254) of the heart (256). The device (200) is navigated through the aortic valve (258) into the aortic root (260) along a previously introduced guide wire (262). Once the device (200) has been navigated into the aortic root (260), inflating fluid is conveyed to the inflatable insertion devices (208) so as to inflate the inflatable elements (212). The elements (212) are preferably inflated to a pressure of about 15 bar. Alternatively, the inflatable elements may of course also be inflated while in the ventricle and the device then simply navigated through the aortic valve.

The device (200) is then retracted until the inflatable elements (212) hook or locate in the cusps of the aortic valve (258) leaflets, thus identifying where valve deployment is to take place. In this way the location of the natural heart valve may effectively be determined by simply using tactile feedback. Of course, in addition to tactile feedback, imaging techniques such as fluoroscopy may also be used to assist the clinician in locating and confirming the location of the natural heart valve.

Once the location has been determined, the length of each inflatable element (212) may be independently varied by withdrawing the associated elongate member and thereby shortening the element (212). In order to facilitate shorting of the element, the pressure within the element (212) may have to be reduced slightly, typically to about 10 bar. It will be appreciated that by shortening the individual elements (212), the catheter may be moved relative to the aortic annulus so as to ensure that the catheter is concentric with the aortic annulus.

When the aortic valve (258) has been located and the catheter has been moved relative to the annulus so as to ensure that it is concentric therewith, inflating fluid is introduced into the valve deployment device (218) causing it to expand and thereby deploy the valve (202). Since the inflatable elements (212) are located between the valve (202) and the sidewalls of the aortic root (260) they may be pinched or sandwiched therebetween once the valve (202) has been deployed. Since the inflatable elements are located between the valve deployment device and the annulus while the deployment device is in its expanded or deployment condition, small cavities are provided therebetween which permit blood perfusion to the coronaries. It will be appreciated that since blood perfusion is permitted, the deployment device to remain within the annulus in its expanded or deployed condition for longer.

In order to remove the device (200), the pressure within the inflatable elements (212) is reduced to approximately 3 bar by deflating the elements (212). Each element (212) is then withdrawn by withdrawing the elongate member associated therewith. As described above, withdrawing of the inflatable elements (212) through and into themselves eliminates any shear forces that may normally develop between surfaces. As such, it will be appreciated that no shear forces will develop between the inflatable elements (212) and the deployed valve (202) or the inflatable elements (212) and the sidewalls of the aortic root (260), thereby negating the risk of valve embolization. As described above with reference to FIGS. 10A to 10O, the withdrawal of an inflatable element by invaginating the element onto itself permits the removal thereof without resulting in any relative movement between the inflatable element and a surrounding structure, in this case, the sidewalls of the aortic root and the deployed valve. There is accordingly no risk that removal of the inflatable elements may cause the deployed valve to shift or embolize.

Once the inflatable elements (212) have been completely removed from their pinched position, the pressure is completely removed so as to fully deflate the elements (212). Thereafter the inflation fluid in the deployment device (218) is removed causing the spiralled balloon to collapse. This may of course also be done prior to reducing the pressure within the inflatable elements (212). Thereafter the device (200) is removed through the transapical port and the replacement valve (202) takes over the function of the natural heart valve.

Importantly, the elongate member is selected to be more flexible than the inflatable element when it is pressurized and in its inflated condition and in its desired pre-set shape. Thus, when it has been pressurised, the inflatable member becomes more rigid and less flexible than the elongate member. This may assist the inflatable element to retain its pre-set desired shape during withdrawal of the distal end to the proximal end, when the pressure within the inflatable element has been reduced but is still high enough to retain it in its pre-set shape. The reduced pressure is selected to be sufficiently high to enable the inflatable element to retain its pre-set shape yet low enough to permit withdrawal thereof whilst in position between an anatomical structure, such as a valve root, and a device, such as valve. In the inflated condition, the structure of the inflatable member is provided by the pressure therein retaining it in the pre-set shape. This allows the inflatable element to maintain its structure to avoid buckling, collapsing or crumbling during withdrawal. If the elongate member is not more flexible than the inflatable element in the inflated state, movement of the elongate member may cause the inflatable member to deform by buckling, bending, collapsing, crumbling or the like, which may be undesirable during operating procedures.

Throughout the specification and claims unless the contents requires otherwise the word 'comprise' or variations such as 'comprises' or 'comprising' will be understood to imply the inclusion of a stated integer or group of integers but not the exclusion of any other integer or group of integers.

The invention claimed is:

1. A system for delivery of a medical implant comprising: at least two inflatable insertion devices capable of being percutaneously introduced into a patient's body, each of said inflatable insertion devices comprising an inflatable element in the form of a small diameter elongate tube having a distal end and a proximal end and being operable between a collapsed condition and an inflated condition, wherein an elongate member extends internally of the inflatable element from the distal end thereof and which is capable of being withdrawn towards the proximal end of the inflatable element to result in the distal end being withdrawn towards the proximal end internally of the inflatable element, and wherein the entire inflatable element is a non-compliant inflatable element and pre-set to a desired elongate shape so as to adopt the pre-set elongate shape when inflated, and wherein the elongate member is more flexible than the inflatable element when inflated to its pre-set desired elongate shape such that when the distal end is withdrawn towards the proximal end internally of the inflatable element, the inflatable element decreases in length while maintaining the pre-set elongate shape to remove shear forces from the inflatable element.

2. A system for delivery of a medical implant as claimed in claim 1, wherein the pre-set shape includes any suitable elongate shape including a hook-like, straight bent, spiral or semi-circle.

3. A system for delivery of a medical implant as claimed in claim 1, wherein the device includes an inflation tube at or near the proximal end of the inflatable element through which inflating fluid may be introduced into the inflatable element.

4. A system for delivery of a medical implant as claimed in claim 3, wherein the elongate member extends through the proximal end of the inflatable element and through the inflation tube.

5. A system for delivery of a medical implant as claimed in claim 3, wherein the inflatable element and the inflation tube are integrally manufactured.

6. An inflatable insertion device as claimed in claim 1, wherein the elongate tube has a varying diameter along its length.

7. An inflatable insertion device as claimed in claim 1, wherein the inflatable element is capable of resisting pressures within the range from about 5 bar up to about 50 bar.

8. A system for delivery of a medical implant as claimed in claim 1, wherein the elongate member is capable of withdrawing the entire inflatable element through the proximal end thereof.

9. A system for delivery of a medical implant as claimed in claim 1, wherein the elongate member and the inflatable element are manufactured integrally.

10. A system for delivery of a medical implant as claimed in claim 1, wherein the elongate member is manufactured from linen, hemp, silk, nylon, vectran or prolene.

11. A system for delivery of a medical implant as claimed in claim 1 wherein the elongate member is secured to the distal end of the inflatable element by means of an adhesive, ultrasonic welding, thermal bonding, or by forming a knot about a portion of the inflatable element material.

12. A system for delivery of a medical implant as claimed in claim 1, wherein the inflatable element is manufactured from heat shrink materials selected from polyethylene terephthalate (PET) in particular, polyolefin, polytetrafluoroethylene (PTFE), fluorinated ethylene propylene (FEP), perfluoroalkoxy (PFA), ethylene tetrafluoroethylene (ETFE), polyester, polyether ether ketone (PEEK), polyvinyl chloride (PVC) or combinations thereof.

13. An inflatable insertion device capable of being percutaneously introduced into a patient's body, the device comprising an inflatable element in the form of a small diameter elongate tube having a distal end and a proximal end and being operable between a collapsed condition and an inflated condition, wherein an elastic elongate member extends internally of the inflatable element from the distal end thereof and which is capable of being withdrawn towards the proximal end of the inflatable element to result in the distal end being withdrawn towards the proximal end internally of the inflatable element, and wherein the entire inflatable element is a non-compliant inflatable element and pre-set to a desired elongate shape so as to adopt the pre-set elongate shape when inflated, and wherein the elongate member is more flexible than the inflatable element when inflated to its pre-set desired elongate shape such that when the distal end is withdrawn towards the proximal end internally of the inflatable element to enable withdrawal of the inflatable element when in the inflated condition without causing it to deform.

* * * * *